United States Patent [19]

Christ et al.

[11] 4,264,740
[45] Apr. 28, 1981

[54] APPARATUS FOR TREATING RESIDUAL WATER

[75] Inventors: Charles Christ, Connerre; Jean M. Lebeault, Villers, Coudun; Claude Noel; Joseph Leclair, both of Compiegne, all of France

[73] Assignee: Christ Fils S.A., Connerre, France

[21] Appl. No.: 931,380

[22] Filed: Aug. 7, 1978

[30] Foreign Application Priority Data

Aug. 8, 1977 [FR] France .............................. 77 24342

[51] Int. Cl.$^3$ ............................................ C12M 1/36
[52] U.S. Cl. .................................. 435/289; 99/277.2; 210/178; 210/208; 435/291; 435/315; 435/316
[58] Field of Search ............... 435/316, 287, 289, 290, 435/291, 255, 315; 210/178, 182, 208; 99/276, 277, 277.2

[56] References Cited

U.S. PATENT DOCUMENTS

| 3,384,491 | 5/1968 | Guenther et al. | 435/316 |
| 3,462,275 | 8/1969 | Bellamy | 435/804 |
| 3,809,618 | 5/1974 | Muller | 435/316 |
| 4,097,339 | 6/1978 | Marwil | 435/289 |

OTHER PUBLICATIONS

"Use of Yeast in the Treatment of Sauerkraut Wastes", Chemical Abstracts, vol. 84, #18, 3 May 1976.
Bailey et al., Biochemical Engineering Fundamentals, "Biochemical Reactors, Substrates, and Products", pp. 574–627, McGraw-Hill Book Co., 1977.
Aiba et al., Biochemical Engineering, "Operation, Measurement and Control", pp. 245–279, Academic Press, New York 1965.

Primary Examiner—Raymond N. Jones
Assistant Examiner—George C. Yeung
Attorney, Agent, or Firm—Merchant, Gould, Smith, Edell, Welter & Schmidt

[57] ABSTRACT

This disclosure relates to an installation for treating residual water, particularly residual water resulting from the manufacture of sauerkraut, in order to transform such water into proteinic food products, especially yeasts. The novel installation comprises a fermentation vat, means for supplying said vat with residual water, nutritive salts and oxygen, means for evacuating the contents from the vat, in the form of paste and for feeding the latter to a centrifugal separator, connected to the storage tank for the paste previous concentrated in said separator, said vat further comprising a stirrer in its lower part and a foam separator in its upper portion and a cooling circuit extending through said vat, said installation being also provided with means for adjusting the pH of the medium submitted to fermentation.

1 Claim, 1 Drawing Figure

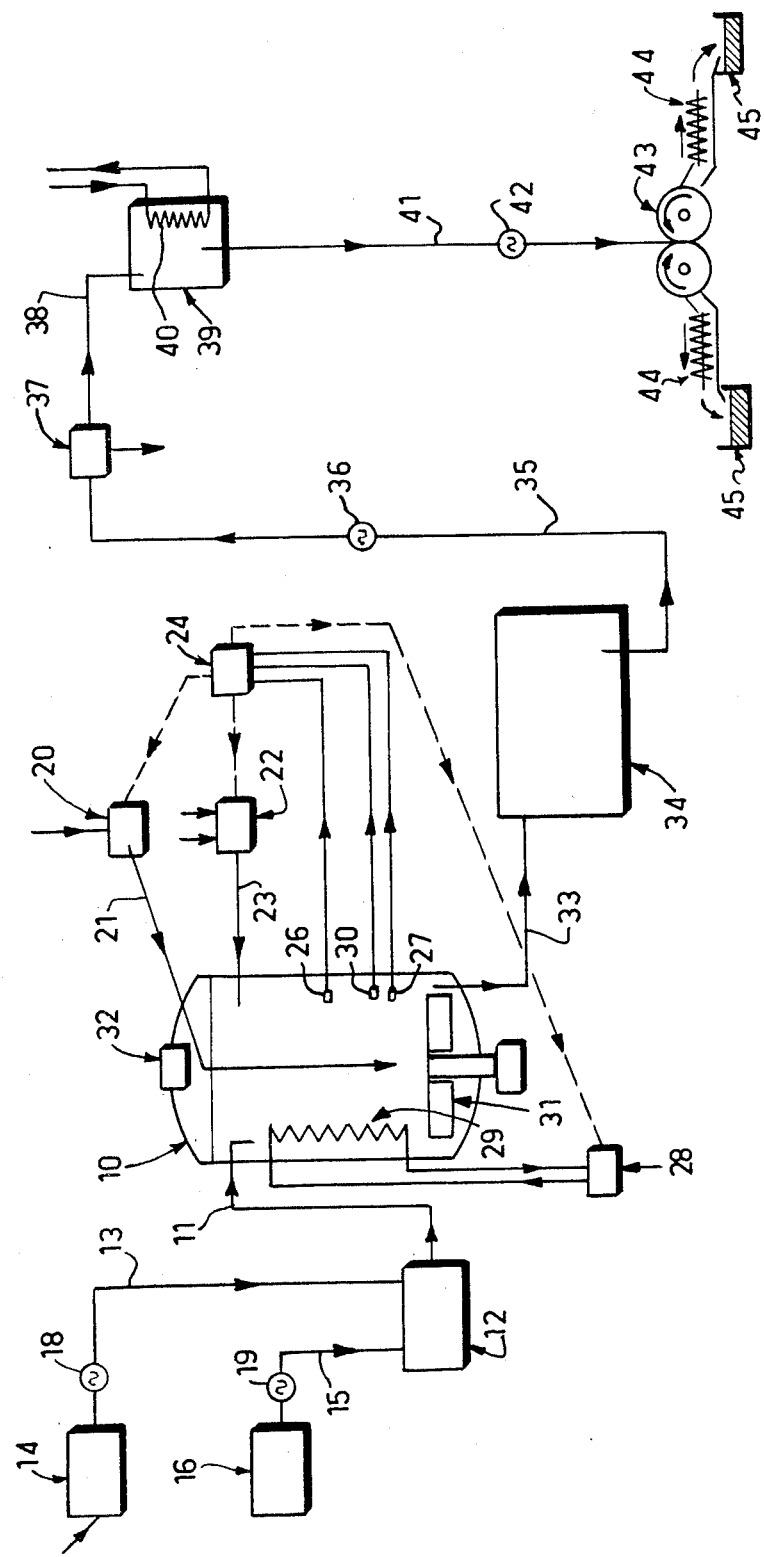

APPARATUS FOR TREATING RESIDUAL WATER

The present invention is related to an installation for treating residual water, especially residual water resulting from the manufacture of sauerkraut, in order to transform said water into proteinic food products.

It should be noted that as far as the treatment of residual water resulting from the manufacture of sauerkraut is concerned, by way of example, about 19.50 tons of residual water are obtained per 100 tons of cabbage.

The composition of the residual water varies from one factory to another, but generally speaking the B.O.D. (biochemical oxygen demand) produced per ton of fermented cabbage varies between 6 and 7 kg. Recent research work has shown that yeast can grow on such residual water, the average yield being 0.65 kg of yeast per kilo of B.O.D.

Such a treatment of residual water not only solves pollution problems, which in the case of sauerkraut residual water are particularly difficult to overcome (as the latter has a high content of sodium chloride, a high B.O.D. value and acid pH), but also leads to the recovery of proteins which can serve as food for livestock, as well as food for human beings at the cost of supplementary treatments.

One of the main objects of the present invention is to provide an installation which allows the industrial treatment of residual water and its transformation into proteinic food stuff, particularly in the case of residual water from sauerkraut, by promoting the development of yeasts such as *Candida utiles*.

The installation according to the present invention for treating residual water, particularly residual water resulting from the manufacture of sauerkraut comprises a fermentation vat, means for supplying this vat with residual water, nutritive salts and oxygen, means for evacuating the contents from the vat, in the form of paste and for feeding the latter to a centrifugal separator connected to a storage tank for the paste previously concentrated in said separator, said vat further comprising a stirrer in its lower part and a foam separator in its upper part, a cooling circuit extending through said vat, said installation furthermore being provided with means for adjusting the pH of the medium submitted to fermentation.

According to one embodiment of the invention, the installation further comprises actuating means adapted to act on the pH adjusting means in response to a pH gauge, on a booster which supplies the vat with oxygen, in response to a gauge for measuring the oxygen content, and on the flow rate of the cooling medium in said cooling circuit, in response to a temperature gauge, said gauges being located in the fermentation vat.

Other features of the invention will become apparent from the following description, given by way of example, with reference to the single appended FIGURE, which illustrates schematically one embodiment of the installation according to the invention.

In the embodiment described and shown, the installation comprises a fermentation vat 10 fed, through a static mixer 12 and a feeding conduit 11, with a mixture introduced into said mixer by means of a conduit 13 connected to a storage tank 14, said mixture containing residual water and various nutritive salts fed into the same mixer through the conduit 15 from a tank 16. Metering pumps 18 and 19 provided respectively on the conduits 13 and 15 feed the mixture to the vat or reactor 10. A small quantity of yeast may be initially supplied, from which growth takes place in the equipment.

The yeast growth depends particularly upon the pressure and temperature conditions, or on the oxygen concentration and the pH of the reaction medium. Satisfactory growth of yeast as a biomass has been found to occur at one atmosphere of pressure and at temperatures between 20° and 38° C., particularly 28°-30° C.

The installation comprises an air booster 20 which feeds air into fermentation vat 10 via a conduit 21, and thus ensures the supply of oxygen necessary for the growth of the yeast. While a batch process will be described, it is understood that the invention can readily be practiced as a continuous process.

In order to control the pH of the reaction medium, a control device 22 is adapted to discharge ammonium hydroxide or phosphoric acid, which ever need be, into reactor 10 via a conduit 23.

This control device 22 is controlled by a control cabinet 24 which receives information from a pH gauge 27 provided in the fermentation vat 10.

This control cabinet also acts upon booster 20 under the action of a gauge 26, which measures the oxygen content, and upon the flow rate of cooling fluid in a cooling device 28, comprising a cooling circuit 29 which penetrates fermentation vat 10 in order to maintain the fermentation temperature constant, in response to information or signals received from a temperature gauge 30, which is located in the vat and connected to the control cabinet.

Fermentation vat 10 is further equipped with an agitator, or stirrer, 31 provided in its lower portion and driven by a motor, as well as a foam separator 32 provided in the upper portion of the vat.

The fermented mixture is discharged from the vat, in the form of paste, into conduit 33 and is stocked in a de-foaming vat 34. The collected paste is then fed through conduit 35 under the action of a volumetric pump 36 to a centrifugal separator 37, in which the paste is concentrated. The thus concentrated paste is discharged into a storage tank 39 through conduit 38, comprising a cooling circuit 40, then is pumped by a pump 42 through a conduit 41 onto a drum drier 43, provided with conveying means in order to fill the dry yeast into containers, bags, or barrels.

As indicated herein above, the described installation for treating residual water is particularly adapted to be used for the treatment of residual water obtained when manufacturing sauerkraut. However, the invention is not limited to the described embodiments, numerous variants may be envisaged particularly as regards the reaction vat and its accessories, as well as the means for collecting the yeast.

Provided that a few modifications and additions are made to the described installation, the latter may be used alternately for the manufacture of vinegar by fermentating alcohol. Such an alternative use for example in a preserve plant which, according to the seasons, manufactures sauerkraut or cans gherkins can give rise to increased productivity of the installation and lead to its accelerated amortization.

Another object of the present invention is a process for reducing residual water resulting from the manufacture of sauerkraut, which process is carried out in a single stage fermentation vat by transforming the organic matter carried by the effluent into a biomass adapted to be used for alimentory purposes. The yield of such reduction is about 90 to 95%.

What is claimed is:

1. An apparatus for treating residual water resulting from the manufacture of sauerkraut so as to derive therefrom proteinic food products, especially yeast, said installation comprising in combination:
   a fermentation vat having an agitator at the bottom thereof and a foam separator at the top thereof;
   separate storage tanks for residual water and for a nutritive fluid;
   means for supplying a mixture of said residual water and nutritive fluid to said fermentation vat, including a static mixer connected to said vat and means including separate metering devices severally metering the residual water and nutrient fluid to said static mixer;
   means for simultaneously controlling conditions within said fermentation vat affecting the growth of yeast therein, including first means responsive to the temperature in said vat and a variable cooling circuit controlled in accordance with the response of said first responsive means, second means responsive to the oxygen content in said vat and an air booster located outside of said fermentation vat and controlled in accordance with the response of said second responsive means, and third means responsive to the hydrogen ion concentration in said vat and means variably dispensing hydrogen ion concentration modifying materials through said vat in accordance with the response of said third responsive means;
   and means enabling discharge of fermented materials from said fermentation vat, including a discharge conduit, a defoaming vat connected to said discharge conduit, a centrifugal separator, means for transporting materials from said defoaming vat to said centrifugal separator, a storage tank connected to receive the concentrated output of said separator, means for cooling the contents of said storage tank, a drum dryer, means transporting material from said storage tank to said drum dryer, and conveyor means transporting dried output material from said drum dryer.

* * * * *